(12) United States Patent
Sellers (10) Patent No.: US 6,423,069 B1
(45) Date of Patent: *Jul. 23, 2002

(54) ORTHOPEDIC SYSTEM HAVING DETACHABLE BONE ANCHORS

(75) Inventor: Timothy M. Sellers, Wayne, PA (US)

(73) Assignee: Synthes (USA), Paoli, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/274,698

(22) Filed: Mar. 23, 1999

(51) Int. Cl.$^7$ .............................................. A61B 17/56
(52) U.S. Cl. ........................... 606/71; 606/69; 606/77; 606/105
(58) Field of Search .......................... 606/69, 70, 71, 606/77, 57, 105, 76, 93

(56) References Cited

U.S. PATENT DOCUMENTS

| | | | |
|---|---|---|---|
| 3,604,414 A | 9/1971 | Borges | 128/92 |
| 4,550,449 A | 11/1985 | Tunc | 623/16 |
| 5,013,315 A | 5/1991 | Barrows | 606/71 |
| 5,147,358 A | 9/1992 | Remmler | 606/57 |
| 5,152,687 A | 10/1992 | Amino | 433/173 |
| 5,201,733 A | 4/1993 | Etheredge, III | 606/53 |
| 5,275,601 A | 1/1994 | Gogolewski et al. | 606/72 |

(List continued on next page.)

FOREIGN PATENT DOCUMENTS

| | | | | |
|---|---|---|---|---|
| DE | 94 01 911 U | 6/1994 | | |
| DE | 297 16 635 | 10/1997 | | |
| EP | 0 073 455 | 3/1983 | | |
| EP | 0390613 A1 | 10/1990 | ........... | A61B/17/08 |
| EP | 0530585 A2 | 3/1993 | ........... | A61B/17/58 |
| EP | 0815878 A2 | 1/1998 | ........... | A61L/31/00 |
| EP | 0818183 A2 | 1/1998 | ........... | A61C/8/00 |

OTHER PUBLICATIONS

Cohen, "Craniofacial Distraction with a Modular Internal Distraction System: Evolution of Design and Surgical Techniques," Plastic and Reconstructive Surgery, vol. 103, No. 6, May 1999, pp. 1592–1607.

Cohen, "A New Modular Internal Distraction System (MIDS) for Mandibular, Maxillary, and Midface Distraction," Abstract of presentation planned to be made at the 55th Annual Meeting of the American Cleft–Plate–Craniofacial Association, Baltimore, Maryland, Apr. 20–25, 1998.

K. Bessho Et Al.: "A Bioabsorbable Poly–L–Lactide Miniplate and Screw system for Osteosynthesis in Oral and Maxillofacial Surgery" vol. 55, 1997, pp. 941–945.

Primary Examiner—David O. Reip
Assistant Examiner—Julian W. Woo
(74) Attorney, Agent, or Firm—Pennie & Edmonds LLP (57) ABSTRACT

The present invention provides an improved orthopedic system in which the part of the device that attaches to the bone is detachable from the parts of the device which provide the bone stabilization, distraction, etc. In a preferred embodiment, the system includes a proximal bone plate and associated proximal fastener, and a distal bone plate and associated distal fastener. The bone plates are affixed to the bone on opposing sides of the bone repair site, which may be an osteotomy. The fasteners serve to mechanically couple the orthopedic device, which may be a distractor, through the bone plates, to the bone. The fasteners are releasably mechanically coupled to the bone plates. This releasability permits the distractor and fasteners to be removed after the orthopedic procedure is complete, leaving only the bone plates in the patient. The bone plates may be made with a low profile, such that they may be left permanently in the patient. In a preferred embodiment, the bone plates are made from a resorbable material, such that they will be absorbed by the patient's body. Methods for using this novel orthopedic system are also disclosed.

15 Claims, 5 Drawing Sheets

U.S. PATENT DOCUMENTS

| | | | |
|---|---|---|---|
| 5,364,396 A | 11/1994 | Robinson et al. | 606/53 |
| 5,470,334 A | 11/1995 | Ross et al. | 606/72 |
| 5,484,439 A | 1/1996 | Olson et al. | 606/65 |
| 5,522,817 A | 6/1996 | Sander et al. | 606/72 |
| 5,540,687 A | 7/1996 | Fairley et al. | 606/60 |
| 5,569,248 A | 10/1996 | Mathews | 606/61 |
| 5,622,493 A | 4/1997 | Razdolsky et al. | 433/7 |
| 5,713,903 A | 2/1998 | Sander et al. | 606/72 |
| 5,735,688 A | 4/1998 | Razdolsky et al. | 433/7 |
| 5,775,907 A | 7/1998 | Razdolsky | 433/173 |
| 5,807,382 A * | 9/1998 | Chin | 606/71 |
| 5,827,286 A * | 10/1998 | Incavo et al. | 606/71 |
| 5,829,971 A | 11/1998 | Razdolsky et al. | 433/7 |
| 5,855,580 A * | 1/1999 | Kreidler et al. | 606/71 |
| 6,113,599 A * | 9/2000 | Lansberger | 606/57 |

* cited by examiner

ORTHOPEDIC SYSTEM HAVING DETACHABLE BONE ANCHORS

TECHNICAL FIELD

The present invention relates to an orthopedic system and, more particularly, to an improved orthopedic system wherein the part of the device that attaches to the bone is detachable from the parts of the system which provide the bone fixation, reduction, distraction, etc.

BACKGROUND OF THE INVENTION

A variety of orthopedic devices, including bone fixation, reduction, and distraction devices, are known in the art. Fixation devices, or fixators, are used to stabilize bone segments and to facilitate the healing of bones at a bone repair site. As used herein "bone repair site" refers to any bone region which is bounded on opposing sides by relatively healthy bone regions to which orthopedic devices can be secured, such as an osteotomy or a fracture. Reduction and distraction devices (commonly referred to as reducers and distractors), are used to gradually adjust the relative orientation and spacing of the bone parts on opposing sides of a bone repair site.

Fixators generally consist of transcutaneous pins or screws secured in the bone on either side of the bone repair site. An adjustable external fixation mechanism is attached to the pins, allowing the relative positions of the pins to be adjusted, thus aligning the bone regions across the bone repair site. When the desired alignment is achieved, the fixation mechanism is locked in place to maintain the alignment. After the bone repair site has healed, the fixator is removed from the patient.

Reducers and distractors typically have structure similar to fixators, except that they additionally include a mechanism which allows controlled incremental adjustment of the distance between parts of the device on opposing sides of the bone repair site. Typically, distractors are used to perform distraction osteogenesis. This procedure was perfected by the Russian orthopedic doctor, Gavriel Ilizarov. A typical procedure of this type involves at most an osteotomy completely separating the bone into two segments, or at least an incision of the cortical portion of the bone. Then, the bone segments on either side of the osteotomy (or the medullary or cancellous portion of the bone on either side of the incision) may be expanded. This gradual separation allows new bone to form in the osteotomy void. The distraction phase is followed by a consolidation phase, during which the distractor is held fixed, and the new bone growth gains strength. Following the consolidation phase, the distractor is removed from the patient.

The design of the early fixators and distractors, which used bone pins and screws to attach the device to the bone are known to have certain problems. For example, numerous pins are needed to attach a single device; at a minimum, two pins are required, but typically, many more are used. Each pin involves a transcutaneous incision, thus multiplying the risk of infection to the patient. Furthermore, a pin clamp or coupling is required to join the fixation/distraction mechanism to the pins, and the design and operation of these couplings are complicated by the difficulty in aligning the pins accurately when they are inserted into the bone. Finally, because the pins extend in a generally perpendicular direction from the insertion site, they cause the resultant overall device to stick out quite far from the patient's body (i.e., the device has a high profile), and the device is unsightly. A high-profile device is more subject to bumps and snags than one which is completely located close to the patient's body. Such seemingly aesthetic considerations are also important because a high-profile device may be rejected by prospective patients, especially children.

Accordingly, more recent devices have been designed not to use transcutaneous pins for attachment to the bone, but rather to use more low-profile bone anchors, such as plates with screw holes, as part of a low-profile overall device. This improved prior art is exemplified by U.S. Pat. No. 5,364,396 to Robinson et al. ("the Robinson patent"), which discloses an implantable bone distraction device which includes low profile blocks for attachment to osteotomically separated bone sections. The entire device can be implanted subcutaneously, except for a transcutaneous actuator assembly which is linked to the implanted distraction assembly, and allows adjustment of the distraction distance from outside the patient's body.

However, modern low-profile fixation/distraction systems such as that disclosed in the Robinson patent suffer from the drawback that their use necessitates two substantial, invasive, surgical procedures: one to implant the device, and another to remove it after the fixation/distraction procedure is complete. Unnecessary surgical procedures are of course undesirable, based on both considerations of health care costs and the medical risks associated with surgery.

Accordingly, there is a need in the art to provide a low-profile fixator/distractor that does not require a second surgical procedure to remove the device after the fixation/distraction procedure is complete. Indeed, there is a need in the orthopedic device art more generally, to provide a device that does not require a second surgical procedure to remove the device after the orthopedic procedure is complete.

SUMMARY OF THE INVENTION

The present invention addresses the need in the art by providing an orthopedic device, such as a bone fixator, reducer, or distractor, with detachable bone anchors, such that after the completion of the orthopedic process, the orthopedic device can be remotely disengaged, from outside the patient, from the subcutaneous bone anchors, leaving only the subcutaneous bone anchors implanted in the patient.

The orthopedic system of the present invention includes at least two bone anchors. Each of these anchors has a bone-contacting surface and fastener-connecting portion. There is a fastener associated with each bone anchor; the fastener includes a device-connecting portion for connection to an orthopedic device (such as a distractor), and a anchor-connecting portion for establishing a releasable mechanical coupling with the fastener-connecting portion of the associated anchor. An orthopedic device, such as a distractor, is coupled to the device-connecting portions of each fastener in order to perform the desired procedure. After the orthopedic procedure involving the orthopedic device is complete, the mechanical couplings of the fasteners to the bone anchors can be released, allowing the fasteners and device to be easily removed from the patient without requiring the removal of the bone anchors.

The bone anchors may be in the form of bone plates, and may be made in full or in part from any appropriate bio-compatible material, such as a bio-absorbable (resorbable) material. When formed as bone plate, the anchors may have one or more screw holes adapted to receive a bone screw. The bone screws may also comprise a bio-absorbable material, in which case the material selected for the screws should be such that the screws will take at least as long to be absorbed by the patient's body as the bone plates.

The releasable coupling of at least one of the bone anchors and fastener may comprise a detent mechanism. Preferably, the release of the detent mechanism is prevented when the orthopedic device is substantially fully coupled to the device-connecting portion of that fastener; this avoids undesired release of the system while it is in use. Release of the detent mechanism is permitted when the orthopedic device is at least partially uncoupled from the device-connecting portion of that fastener, such that the system can be disassembled when desired.

One of the fasteners may have an anchor-connecting portion comprising a shoe; in this embodiment, the bone anchor associated with that fastener will have a fastener-connecting portion comprising an engagement cavity. The shoe and cavity are sized and shaped to allow the shoe to be slidingly received by the cavity. The shoe and engagement cavity may have a corresponding substantially rectangular shape, in which case the releasable mechanical coupling of the fastener to the bone anchor is a slip lock. Alternatively, the shoe and the associated engagement cavity have a corresponding substantially tapered shape, in which case the releasable mechanical coupling of the fastener to the bone anchor is a frictional lock.

An orthopedic distraction system for distracting first and second osteotomically separated bone sections according to the present invention may comprise a distal bone plate, a distal fastener, a proximal bone plate, a proximal fastener, and a distraction device. The distal bone plate is designed to be subcutaneously implanted and attached to the first bone section, and is provided with screw holes adapted to receive bone screws, a bone-contacting surface, and a first engagement cavity having a substantially rectangular shape.

The distal fastener associated with the distal bone plate has a device-connecting portion and a shoe. The shoe is shaped and sized to correspond to the first engagement cavity. In this way, when the shoe is slidingly accepted by the first engagement cavity, a slip lock of the distal fastener to the distal bone plate is produced.

The proximal bone plate is also designed to be subcutaneously implanted, and is attached to the second bone section. The proximal bone plate has screw holes adapted to receive bone screws, a bone-contacting surface, and a second engagement cavity. A proximal fastener is provided, to be associated with the proximal bone plate; this proximal fastener has a device-connecting portion and a anchor-connecting portion. The releasable coupling of the proximal bone plate and proximal fastener comprises a detent mechanism. Release of the detent mechanism is prevented when a distraction device is fully coupled to the device-connecting portion of the proximal fastener, but release of the detent mechanism is permitted when the orthopedic device is at least partially uncoupled from the device-connecting portion of the proximal fastener. In use, the distraction device is coupled to the device-connecting portions of each fastener. According to the novel orthopedic system of the present invention, when desired, both fasteners can be released from their corresponding bone plates, allowing the fasteners and distraction device to be easily removed from the patient without requiring the removal of the bone plates.

Also disclosed is a method for treating bone sections on either side of a bone repair site. Bone anchors are attached to the bone on each side of the bone repair site, and fasteners are releasably coupled to each of the bone anchors, an orthopedic device is coupled to the fasteners, either before or after the fasteners are coupled to the anchors. The orthopedic procedure is performed using the orthopedic device, and the orthopedic device and fasteners may be removed. The removal of the orthopedic device and fasteners may be performed in any order. The method disclosed is compatible for use with all of the various embodiments of the novel distraction system described herein.

The method for treating a bone repair site according to the present invention generally comprises the following steps. An incision is made, for access to the bone repair site. One bone anchor is attached to the bone on each side of the bone repair site, and a fastener is releasably mechanically coupled to each of the bone anchors. An orthopedic device is mechanically coupled to the fasteners and is used in performing the desired orthopedic procedure. When the procedure is complete, the orthopedic device and fasteners are removed, in any order, from the patient. The incision is then closed, leaving the bone anchors attached to the bone.

More specifically, the method for treating a bone repair site on a patient according to the present invention comprises the following steps. An incision is made, for access to the bone repair site. A distal bone plate is subcutaneously attached to the bone; this distal bone plate has screw holes adapted to receive bone screws, a bone-contacting surface, and a first engagement cavity having a substantially rectangular shape. A distal fastener is releasably coupled to the distal bone plate, this distal fastener having a device-connecting portion and a first shoe, the shoe being shaped and sized to correspond to the first engagement cavity. The shoe is slidingly accepted by the first engagement cavity, producing a slip lock of the distal fastener to the distal bone plate. A proximal bone plate is subcutaneously attached to the bone, this proximal bone plate has a bone-contacting surface, a second engagement cavity, and screw holes adapted to receive bone screws. A proximal fastener is releasably mechanically coupled to the proximal bone plate; this proximal fastener has a device-connecting portion and a anchor-connecting portion. The releasable coupling of the proximal fastener to the proximal bone plate comprises a detent mechanism. An orthopedic device, such as a distractor, is coupled to the device-connecting portions of both fasteners, and is used to perform the desired orthopedic procedure. After the procedure is complete, the distal fastener is uncoupled from the distal bone plate and the proximal fastener is uncoupled from the proximal bone plate, allowing the fasteners and orthopedic device to be removed from the patient. Finally, the incision is closed, leaving the bone plates in the patient.

BRIEF DESCRIPTION OF THE DRAWINGS

The features and advantages of the present invention will become more readily apparent from the following detailed description of the invention in which like elements are labeled similarly and in which.

DETAILED DESCRIPTION OF THE PREFERRED EMBODIMENTS

The orthopedic device of the present invention is discussed herein with reference to a preferred embodiment adapted to be used in a linear distraction of a mandible. However, it will be clear that the invention is not limited to mandibular distraction, or indeed to distraction generally, but rather finds general application for use with any orthopedic device that involves anchoring devices to bone.

Figure 1:
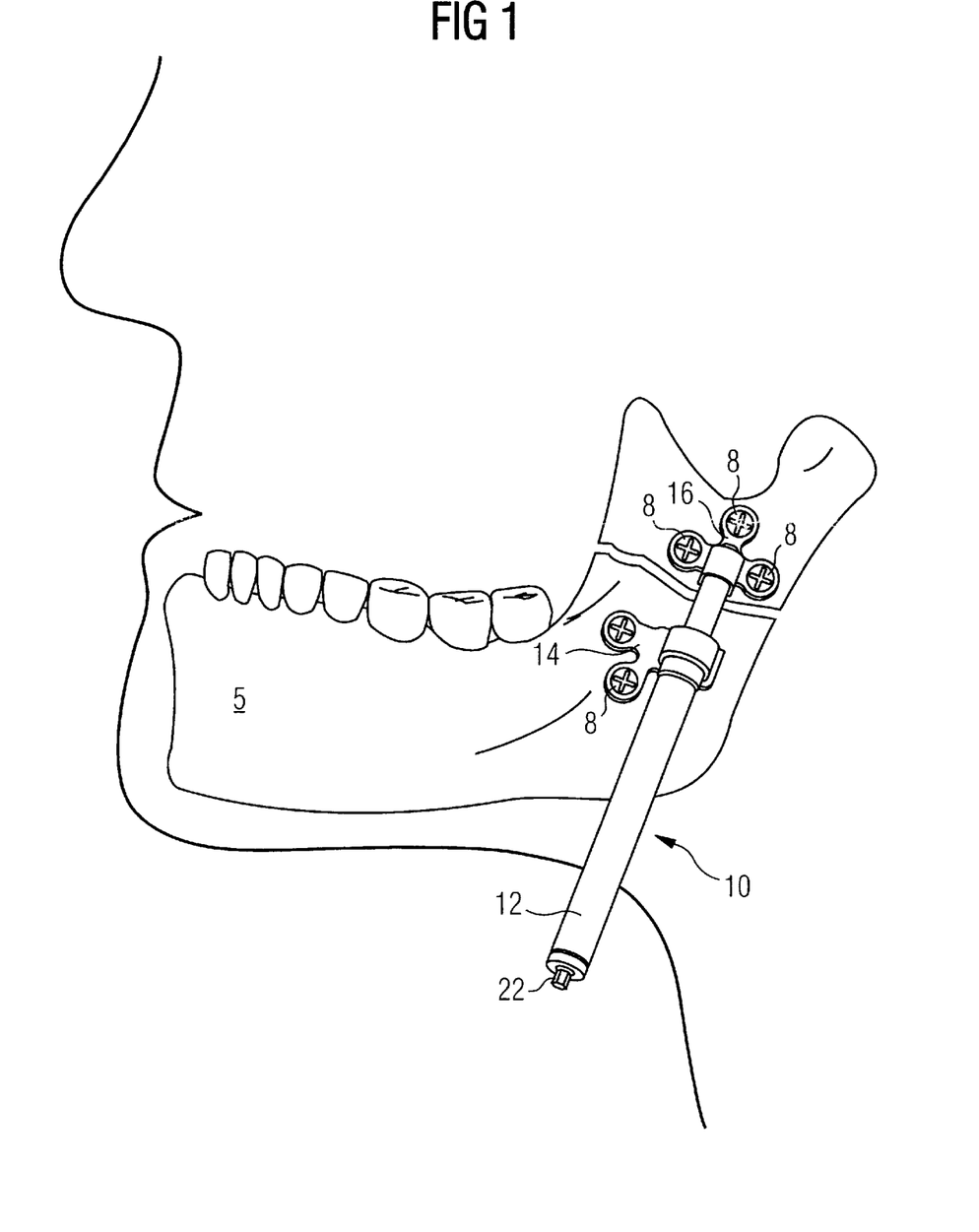
FIG. 1 is a perspective view of an embodiment of the present orthopedic system adapted for use on the mandible, illustrating a distractor attached to osteotomically separated portions of a mandible.
Figure 2:
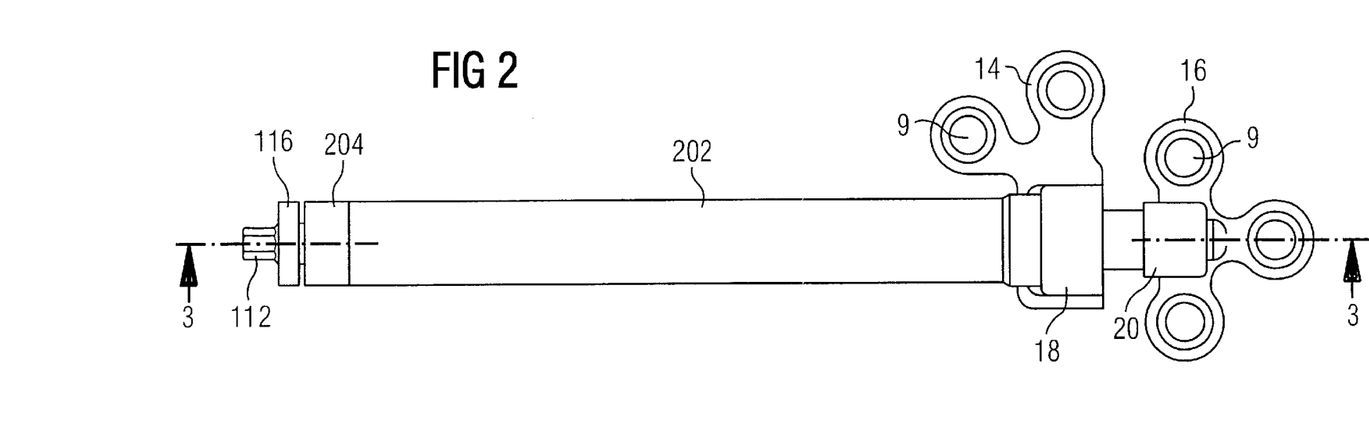
FIG. 2 is a top plan view of the system illustrated in FIG. 1.
Figure 3:
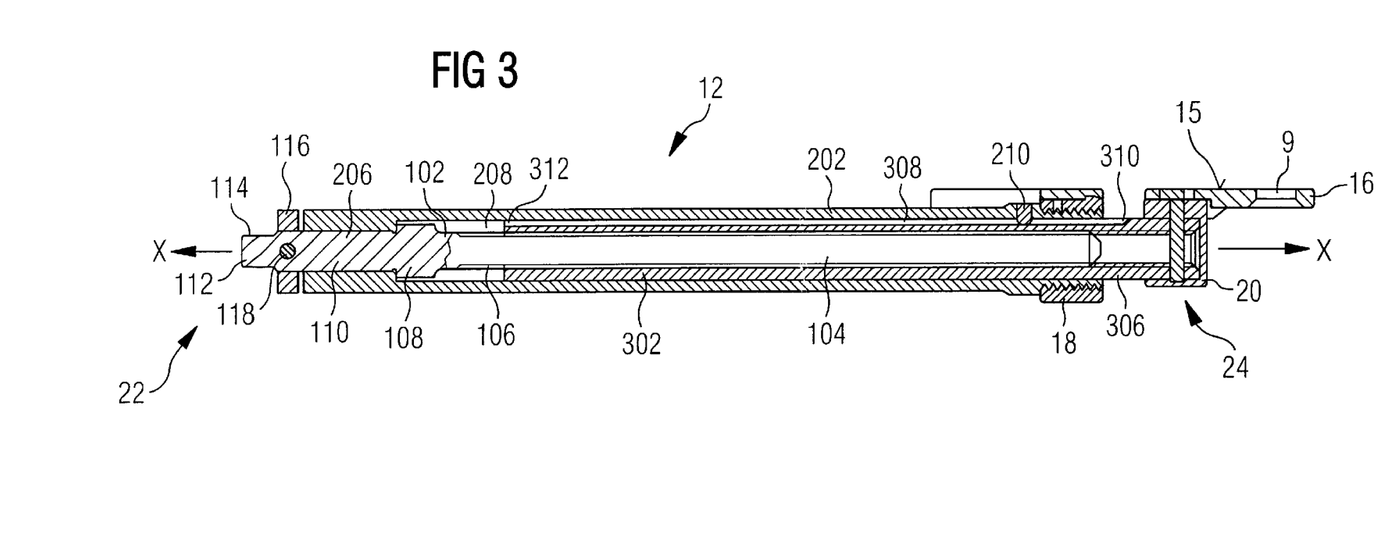
FIG. 3 is a sectional side view of the system illustrated in FIG. 1 taken along line 3—3 in FIG. 2.

As seen in FIGS. 1–3, the orthopedic system 10 generally consists of distraction assembly 12, proximal and distal foot plates (or bone plates) 14 and 16, respectively, and proximal and distal fasteners 18 and 20, respectively. The distraction assembly 12 has a proximal, or adjustment end 22, and a distal end 24. The orthopedic system 10 is affixed to mandible 5 by bone screws 8 which are inserted through screwholes in foot plates 14 and 16. In use, the entire orthopedic system 10 is implanted subcutaneously, except for the adjustment end 22 of the distraction assembly 12, which extends subcutaneously through a small incision in the skin. It will be understood that with reference to the various elements of the present invention, the term proximal is used to refer to the end of the device associated with the proximal end of the distraction assembly that extends outwards transcutaneously, and the term distal is used to refer to the other end of the device.

Turning now to the details of the orthopedic system 10 as best illustrated in FIGS. 2 and 3, the distraction assembly 12 generally consists of a lead screw 102, an outer sleeve 202, and an inner sleeve 302. As described in detail below, lead screw 102 is journaled within in outer sleeve 202, such that screw 102 can rotate, but not translate axially, relative to sleeve 202. Inner sleeve 302 has internal threading which interacts with the external threading 106 on screw 102. Thus, in the assembled distraction assembly 12, rotation of screw 102 is translated to linear motion of the inner sleeve 302, like a nut being driven on a bolt, causing telescopic expansion or contraction of the overall assembly 12.

Lead screw 102 has a distal shaft portion 104 provided with external screw threading 106, an enlarged-diameter intermediate portion 108, a proximal shaft portion 110, and a proximal, or adjustment end 112. Adjustment end 112 is provided with a tool interface 114, such as a hexagonal surface which can be driven a standard hexagonal driving tool. The outer sleeve 202 has two different inside cavity portions. The proximal cavity portion 206 has an inside diameter sized so as to slidably accept the proximal shaft portion 110 of the screw 102. The distal cavity portion 208 has an inside diameter sized so as to slidably accept the inner sleeve 302. Inner sleeve 302 is provided with internal threading that matches the external threading 106 on screw 102, and an exterior surface 306 which is generally smooth except for longitudinal slot 308. Slot 308 extends from the proximal end 310 of the sleeve towards the distal end 312.

Figure 6A:
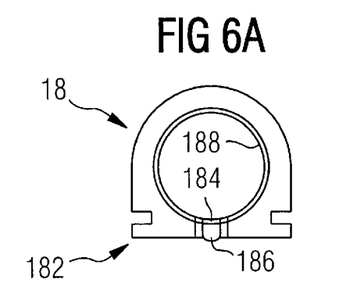
FIGS. 6A and 6B are a side elevation view and a bottom plan view, respectively, of the proximal fastener of the system illustrated in FIG. 1.
Figure 6B:
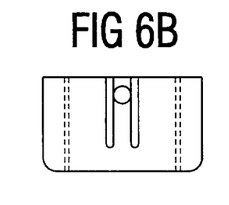
Figure 9:
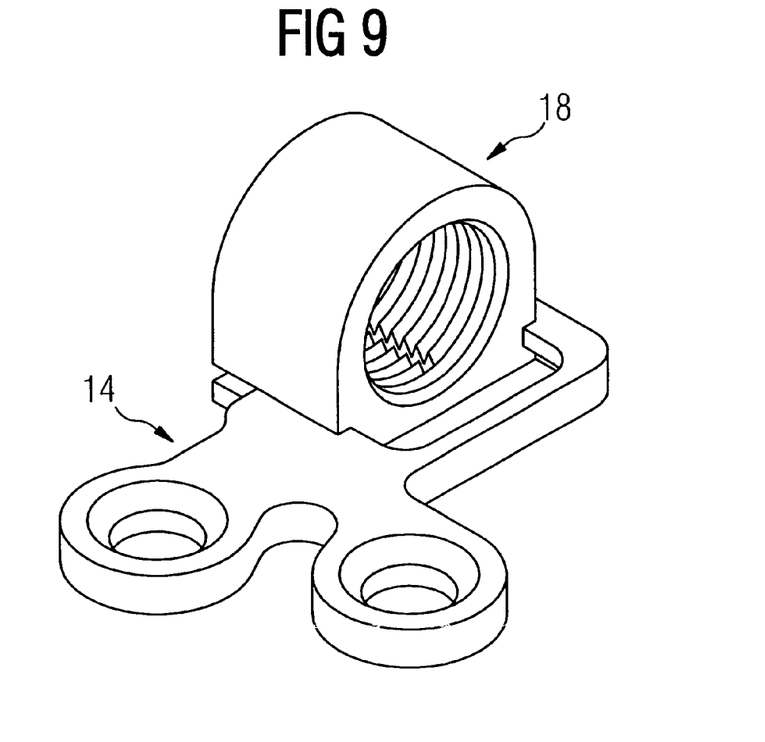
FIG. 9 is a perspective view of the proximal footplate and the proximal fastener which illustrates the fastener partially engaged with the plate.

The proximal fastener 18 is best understood by reference to FIGS. 6A and 6B. It has a device-connecting portion comprising an internally-threaded bore 188 which accepts the external threading on the distal end of the outer sleeve 202. The proximal fastener also has a bone anchor-connecting portion comprising shoe 182. The shoe may have a rectangular shape, as shown in FIG. 6B, or may have a tapered shape, depending on the shape selected for the cavity 142 in proximal bone plate 14. This shoe 182 is provided with a sprung arm 184, on the end of which is a projection 186. The operation of the sprung arm and projection in forming a detent mechanism coupling the fastener 18 to the plate 14 is discussed in detail below. FIG. 9 shows the fastener 18 in an intermediate stage of being releasably mechanically coupled or uncoupled from plate 14.

Figure 7A:
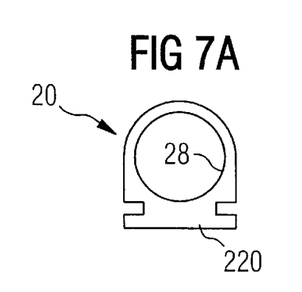
FIGS. 7A and 7B are a side elevation view and a bottom plan view, respectively, of the distal fastener of the system illustrated in FIG. 1.
Figure 7B:
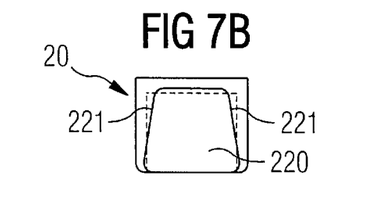
Figure 8A:
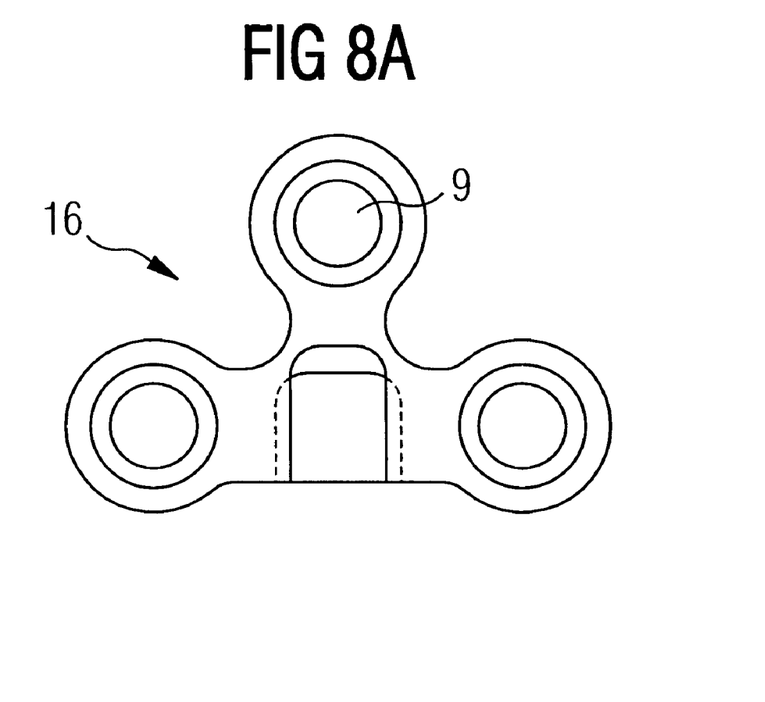
FIGS. 8A and 8B are a side elevation view of a distal foot plate and a bottom plan view of a distal fastener, respectively, in another embodiment of the system illustrated in FIG. 1.
Figure 8B:
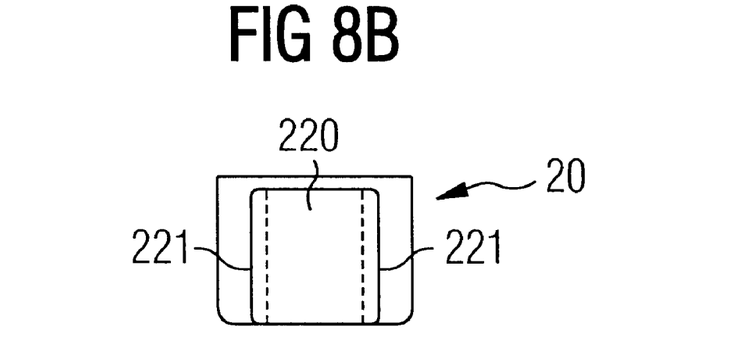
Figure 10:
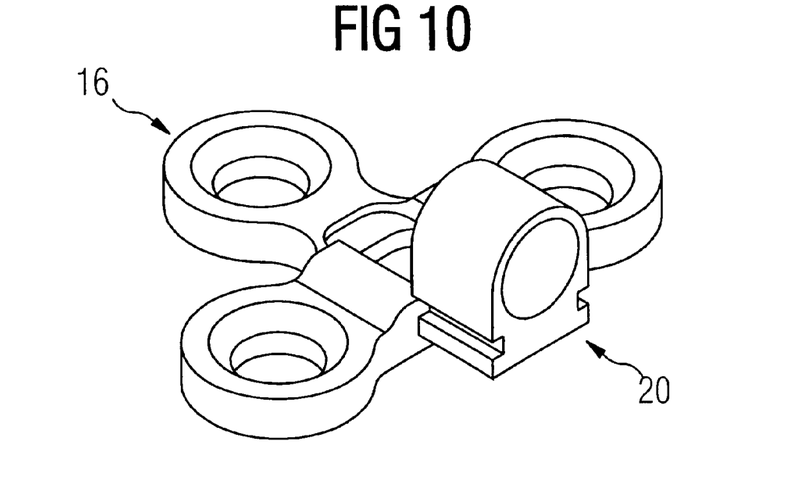
FIG. 10 is a perspective view of the distal foot plate and the distal fastener which illustrates the fastener partially engaged with the plate.

The distal fastener 20 is best understood by reference to FIGS. 7A and 7B. it has a device-connecting portion comprising a bore 28 which accepts the distal end of the inner sleeve 302. The distal fastener also has a bone anchor-connecting portion comprising shoe 220. The shoe may have a substantially rectangular shape, as shown in FIG. 8B, or a substantially tapered shape, as shown in FIG. 7B. The shape of the shoe is selected to correspond to the shape of the cavity 162 in the plate 16. FIG. 10 shows the fastener 20 in an intermediate stage of being releasably mechanically coupled or uncoupled from plate 16.

The proximal shaft portion 112 of lead screw 102 is slideably received within the proximal cavity portion 206 of outer sleeve 202, such that screw 102 is free to rotate relative to the outer sleeve 202. A region of the proximal shaft portion 110, and the adjustment end 112 of screw 102 extend out from the proximal end 204 of the sleeve. A collar 116 is attached to the screw on the extending region of the proximal shaft portion by pin 118. The collar 116 and the enlarged-diameter intermediate shaft portion 108 prevent axial translation of the screw 102 relative to outer sleeve 202. In this way, screw 120 is effectively journaled within the outer sleeve 202.

The internal threading of inner sleeve 302 interacts with the external screw threading 106 of lead screw 102, while at the same time the smooth exterior surface 306 of the inner sleeve is in sliding relation with the smooth inner surface of the proximal cavity portion 208 of outer sleeve 202. In this way, inner sleeve 302 is in sliding, telescoping relation with outer sleeve 202.

Guide pin 210 is press-fit into a hole which extends through the thickness of the outer sleeve 202. The end of the guide pin which extends inwards projects sufficiently beyond the inner surface of the outer sleeve so as to interact with the longitudinal slot 308 provided on the exterior surface of the inner sleeve 302. Thus, it will be appreciated that the interaction of longitudinal slot 308 and guide pin 210 form a keyway which prevents relative rotation of the sleeves about the longitudinal axis X—X of the device (designated X—X in FIG. 3).

Foot plates 14 and 16 serve as the bone anchors, and can be made from any biocompatible material such as metal, plastic, or composites. In a preferred embodiment, the foot plates are bone plates made of a titanium alloy. In an alternative embodiment discussed in more detail below, the foot plates can be made from a bio-absorbable material. The choice of material from which to construct the foot plates is a routine design matter which depends purely on the particular medical application in which the system according to this invention is used.

As shown in FIG. 1, the foot plates are provided with screw holes 9 to accept the bone screws 8 which affix the device to the bone on either side of the patient's bone repair site. These holes are preferably countersunk to reduce the height of projection of the screw heads above the foot plate surface after the device is fully implanted. The foot plates have a bottom, or bone-contacting surface 15 which may be flat or may be shaped to conform to the contours of the bone to which it is being attached.

The distal foot plate 16 is provided with a fastener-connecting portion comprising the slot-like engagement cavity 162 which accepts the shoe 220 of the distal fastener. The engagement cavity may have a substantially rectangular shape. In this case, the side walls 166 of the cavity are parallel with the longitudinal axis X—X of the device, as shown in FIG. 8A, and the shoe 220 has a substantially rectangular shape corresponding to the shape of the cavity 162. The shape and size of the shoe is selected to allow the shoe 220 to be slidingly received by the cavity 162, creating a slip lock of the fastener 20 to foot plate 16. The slip lock is a releasable mechanical coupling which is easily released by the application of a force separating the fastener 20 from foot plate 16.

In an alternate embodiment, the engagement cavity may have a substantially tapered shape, in which case side walls 166 are tapered relative to the longitudinal axis X—X of the device, as shown in FIG. 8A. The shoe 220 in this embodiment has a substantially tapered shape corresponding to the shape of cavity 162. The shape and size of the shoe in this embodiment creates a frictional lock of the fastener 20 to the foot plate 16. The frictional lock is a releasable mechanical coupling, but requires more separating force to achieve the release than does the coupling in the slip lock embodiment described above.

If the device is to be used in the standard distraction procedure (i.e., a procedure in which the device is to apply a tensile force to the bone repair site), then the foot plate is mounted with the open end of the cavity facing the bone repair site, that is, the orientation shown in FIG. 1. In this way, as the distraction device is activated, the distraction force will tend to drive the shoe 220 of the distal fastener 20 into the engagement cavity 162, resulting in a releasable mechanical coupling of the fastener 20 and plate 16 resulting from the interaction of the shoe 220 with the cavity 162. Conversely, if the device were to be used in a compression mode, the foot plate could be mounted with the open end of the cavity facing away from the bone repair site, such that the compression force would tend to produce the above-described coupling.

Figure 5A:
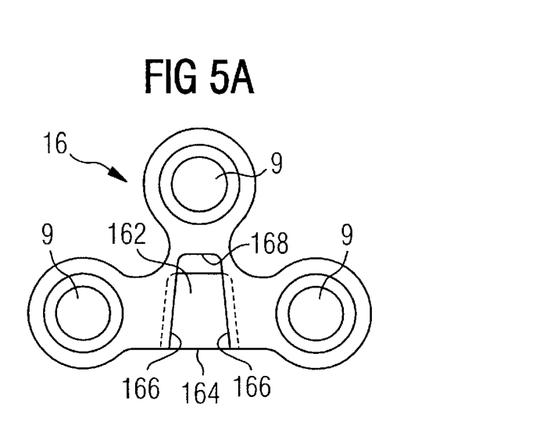
FIGS. 5A and 5B are a top plan view and a side elevation view, respectively, of the distal foot plate of the system illustrated in FIG. 1.
Figure 5B:
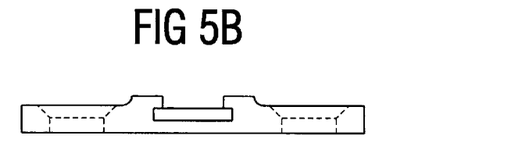

As shown in FIG. 5A, the screw holes of plate 16 are located around the cavity 162. This geometry has been found to provide a good combination of accessibility to the screws and holding strength when the device of the present invention is used in the distraction of a mandible. However, it is to be understood that the location of the screw holes and the contoured shape of the plate 16 as seen in FIG. 5A is not a critical aspect of the present invention; other screw hole placements and plate shapes could be used without departing from the spirit or scope of the present invention.

The proximal foot plate 14 is also provided with a fastener-connecting portion comprising an engagement cavity 142. This engagement cavity may utilize the tapered wall geometry similar to that of the cavity 162 as described above and shown in FIG. 5A, in which case the proximal fastener 18 would have a wedge-shaped shoe similar to that of fastener 20, as shown in FIG. 7B. The activation force applied to the device would then result in a frictional lock providing a releasable mechanical coupling of the fastener 18 to the plate 14. In a preferred embodiment, however, the cavity 142 will utilize side walls 144 which are parallel to the longitudinal axis X—X of the device, and the releasable mechanical coupling will be a slip lock.

This detent mechanism is comprised of parts of the proximal foot plate 14, proximal fastener 18, and also sleeve 202. The bottom surface 145 of the cavity is provided with a depression 147, which may be in the form of a truncated spherical volume section. The shoe 182 of proximal fastener 18 is provided with a naturally sprung arm 184. Arm 184 is provided on its bottom surface with a "bump" or projection 186 complementary to the shape of depression 147. When the shoe 182 is slid into the cavity 142, the projection 186 and depression 147 operate as a detent mechanism to prevent axial separation of fastener 18 from plate 14.

As can be understood from FIG. 6A, when the sleeve 202 is not threaded into the bore 188, the spring arm 184 may deflect upwards such that the projection 186 becomes disengaged from depression 147, thus disengaging the detent mechanism. The force provided by spring arm 184 alone can serve to hold the detent mechanism in the engaged position under low forces. Furthermore, when sleeve 202 is threaded into bore 188, it completely prevents upwards motion of arm 184, thus preventing disengagement of the detent mechanism even when subjected to substantial forces, such as those generated during when the device is removed from the patient. Only when the sleeve 202 is sufficiently unthreaded from bore 188 can the arm 184 again deflect upward sufficiently to allow the detent mechanism to be disengaged, which in turn permits the shoe 182 to slide out of cavity 142. In other words, when the sleeve is screwed into the fastener, it locks the fastener to be plate 14.

Figure 4A:
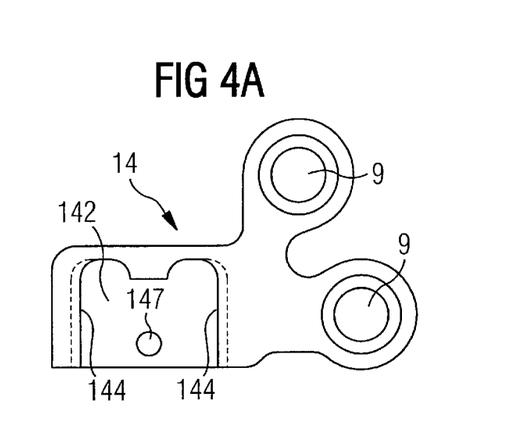
FIGS. 4A and 4B are a top plan view and a side elevation view, respectively, of the proximal foot plate of the system illustrated in FIG. 1.
Figure 4B:
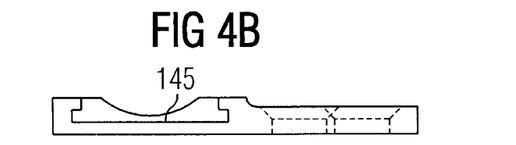

As shown in FIG. 4A, the screw holes of plate 14 are offset both to one side of axial centerline X—X of the device, and are placed such that the plate as a whole takes on the shape similar to an upper case "Y". This geometry has been found to provide a good combination of accessibility to the screws and holding strength when the device of the present invention is used in the distraction of a mandible. However, it is to be understood that the location of the screw holes and the contoured shape of the plate 14 as seen in FIG. 4A is not a necessary part of the present invention; other screw hole placements and plate shapes could be used without departing from the spirit or scope of the present invention.

It is important to note that the fasteners and foot plates of the system of the present invention are separate parts, as opposed to being integrally formed. Furthermore, due to the way in which they are mechanically joined in an conveniently releaseable locked way, they are capable of being separated after the device has served its purpose in the orthopedic procedure—the fasteners and foot plates are not permanently joined, for example by welding, nor are they joined by some other means which would make their separation difficult or inconvenient. Furthermore, the mechanical coupling of the fasteners and foot plates of the present invention does not require any additional parts to achieve the coupling.

In order to use the device of the present invention in a typical distraction procedure, the surgeon makes an incision, performs the distraction, permits consolidation, then removes the distraction assembly, leaving the foot plates affixed to the bone, and closes the incision.

To assemble the system, the lead screw 102 is first inserted into the outer sleeve 202, after the sleeve has first been provided with guide pin 210. The collar 116 is installed on the region of the proximal shaft portion 112 which extends out from the proximal end 204 of the outer sleeve 202. The collar 116 is captivated on the shaft by pressing a pin through matching holes in the collar and proximal shaft portion. The outer sleeve 202 is then threaded into the proximal fastener 18, after the fastener has first been slid into, and lockingly engaged with, foot plate 14 (using the detent mechanism described above). The lead screw 102 is then threaded into inner sleeve 302, care being taken that the longitudinal slot on sleeve 302 is properly engaging with guide pin 210. The distal fastener 20 is then pressed and pinned onto the distal end of the inner sleeve 302, and finally, is engaged with the distal foot plate 16.

To implant the device, a small incision is made of appropriate size to permit access to the bone necessary to attach the foot plates, and in a location appropriately offset from the bone repair site bearing in mind that only the proximal end of the distraction device will extend percutaneously through the incision once implanted. The assembled system is carefully guided into the percutaneous opening and positioned relative to the bone repair site. The foot plates are then affixed to the bone using bone screws, and the incision is closed, with only the proximal end of the device extending percutaneously.

The distraction osteogenesis procedure is performed by turning the lead screw using the tool interface 114. Counterclockwise rotation of the screw will result in axial lengthening of the device, resulting in a distraction force being communicated to the bones through the foot plates.

After the distraction and consolidation phase of the procedure is complete, the device is removed, or disengaged, by reversing the direction of rotation of the lead screw 102. The amount of reverse (i.e., clockwise) rotation depends on the thread pitch of the lead screw, but typically, at least ten full clockwise rotations will be required to cause the distal fastener 20 to disengage from the distal foot plate 16. The sleeve 202 is unthreaded from fastener 18 sufficiently to allow sprung arm 184 to flex, such that when the device is now pushed towards the bone surface, the detent mechanism holding proximal fastener 18 to corresponding proximal foot plate 14 is released, unseating the device from the proximal foot plate. The entire activation portion of the device (lead screw, sleeves, and fasteners) is now disengaged from the patient, and can now be gently removed through the percutaneous port, leaving only the foot plates (and associated bone screws) in the patient. As a final step, the percutaneous port is closed using standard surgical procedures.

In one embodiment of the present invention, the foot plates 14 and 16 may be formed of a bio-absorbable material. Any bio-absorbable material may be used, either natural or synthetic (for example polylactides, polyglycolides, or polyesteramides). By forming the foot plates from a bio-absorbable material, the foot plates may be left in situ after the completion of the distraction osteogenesis. By appropriate selection of the bio-absorbable materials, the foot plates will begin to absorb after their mechanical strength is no longer required for the procedure, and over time the foot plates will substantially or totally be resorbed by the body. By eliminating the need for a second surgical procedure to remove the foot plates, this invention advantageously reduces health care costs as well as the medical risks associated with even the most carefully performed surgery.

In addition, the bone screws 8 used to affix the foot plates to the bone may also be made of bio-absorbable material, either the same material as the foot plates, or a different material. In this case, it may be desirable to select the bio-absorbable materials such that the screws are not absorbed until after the foot plates are substantially absorbed. If the screws were to be absorbed first, this would create the undesirable situation of the foot plates coming loose from the attachment site and being free to migrate subcutaneously.

It should be emphasized that the above described embodiment of the present invention is merely one specific example adapted for a specific application in the human skeletal system. The modifications appropriate for other applications may readily be realized by those who are skilled in the art and who have been equipped with the understanding of the structure and operation of the present invention as set forth in the above description.

For example, the particular linear distractor embodiment shown in FIG. 1 could be used, without any structural modifications, in well-known orthopedic applications other than mandibular distraction; for example it is entirely appropriate for use in the distraction of long bones. In addition, it is evident that various other well-known distraction and fixation assemblies could be substituted for the distraction assembly 12 described above, without departing from the spirit or scope of the present invention. For example, instead of a simple linear distraction assembly, an assembly providing both linear and angular distraction could be provided to bridge the bone repair site and mechanically link the foot plates. Accordingly, it should be understood that the embodiment herein is merely illustrative of the principles of the invention. Various modifications may be made by those skilled in the art which will embody the principles of the invention and fall within the spirit and the scope thereof.

What is claimed is:

1. An orthopedic system for use in an orthopedic procedure comprising:

at least two bone anchors for anchoring the system to a patient's bone, each anchor having a bone-contacting surface and a fastener-connecting portion;

a fastener associated with each of the bone anchors, each fastener having a device-connecting portion and an anchor-connecting portion, the anchor-connecting portion and the fastener-connecting portion of the associated bone anchor providing a releasable mechanical coupling of the fastener to the bone anchor; and an orthopedic device coupled to the device-connecting portions of each fastener;

wherein the anchor-connecting portion of at least one fastener comprises a shoe, and the fastener-connecting portion of the bone anchor associated with that at least one fastener comprises an engagement cavity; wherein the shoe is sized and shaped to be slidingly received by the engagement cavity;

wherein the shoe and the associated engagement cavity have a corresponding substantially tapered shape; whereby the releasable mechanical coupling is a frictional lock;

whereby after the orthopedic procedure is complete, the mechanical coupling of the bone anchors to the fasteners can be released, allowing the fasteners and orthopedic device to be removed from the patient without removal of the bone anchors.

2. The orthopedic system of claim 1, wherein the bone anchors are made of a bio-absorbable material.

3. The orthopedic system of claim 1, wherein the bone anchors are bone plates, each bone plate having at least one screw hole adapted to receive a bone screw to anchor the bone plate to the bone.

4. The orthopedic system of claim 3, wherein the bone plates are made of a bio-absorbable material.

5. The orthopedic system of claim 4, further comprising bone screws made of a bio-absorbable material which takes at least as long as the bone plates to be absorbed in the patient.

6. The orthopedic system of claim 1, wherein the orthopedic device is a distractor.

7. The orthopedic system of claim 1, wherein the releasable coupling of at least one of the bone anchors and the associated fastener comprises a detent mechanism, the release of the detent mechanism being prevented when the orthopedic device is substantially fully coupled to the device-connecting portion of that fastener and release of the detent mechanism being permitted when the orthopedic device is at least partially uncoupled from the device-connecting portion of that fastener.

8. The orthopedic system of claim 1, wherein the orthopedic device is removably coupled to the device-connecting portions of the fasteners.

9. An orthopedic distraction system for distracting first and second osteotomically separated bone sections of a patient, the system comprising:

a distal bone plate for subcutaneous implantation and attachment to the first bone section, the distal bone plate having screw holes adapted to receive bone screws, a bone-contacting surface, and a first engagement cavity having a substantially rectangular shape;

a distal fastener associated with the distal bone plate and having a device-connecting portion and a shoe, the shoe being shaped and sized to correspond to the first engagement cavity; whereby the shoe is slidingly accepted by the first engagement cavity producing a slip lock of the distal fastener to the distal bone plate;

a proximal bone plate for subcutaneous implantation and attachment to the second bone section, the proximal bone plate having screw holes adapted to receive bone screws, a bone-contacting surface, and a second engagement cavity;

a proximal fastener associated with the proximal bone plate and having a device-connecting portion and a bone plate-connecting portion, wherein proximal bone plate and proximal fastener are releasably coupled by a detent mechanism; and an orthopedic device coupled to the device-connecting portions of each fastener;

wherein the release of the detent mechanism is prevented when the orthopedic device is at least substantially fully coupled to the device-connecting portion of the proximal fastener, and release of the detent mechanism is permitted when the orthopedic device is at least partially uncoupled from the device-connecting portion of the proximal fastener, and further wherein both fasteners can be released from their corresponding bone plates, allowing the fasteners and distraction device to be removed from the patient without removal of the bone plates.

10. The orthopedic system of claim 9, wherein the bone plates are made of a bio-absorbable material.

11. The orthopedic system of claim 10, further comprising bone screws made of a bio-absorbable material which takes at least as long as the bone plates to be absorbed in the patient.

12. The orthopedic system of claim 9, wherein the bone plates are made of a bio-absorbable material.

13. The orthopedic system of claim 9, further comprising bone screws made of a bio-absorbable material which takes at least as long as the bone plates to be absorbed in the patient.

14. The orthopedic system of claim 9, wherein the orthopedic device is removably coupled to the device-connecting portions of the fasteners.

15. A method for treating a bone repair site in a patient comprising the steps of:

providing at least two bone anchors, at least one of the bone anchors having an engagement cavity having a substantially tapered shape;

providing a fastener associated with each of the bone anchors, each fastener having a shoe adapted to be slidingly received by the engagement cavity and the shoe having a shape substantially corresponding to the engagement cavity having a substantially tapered shape;

making an incision for access to the bone repair site;

attaching separate bone anchors to the bone on each side of the bone repair site;

releasably mechanically coupling a fastener to each of the bone anchors, this step comprising sliding the shoe into the engagement cavity so that the bone anchors and the fasteners are coupled by friction lock;

coupling an orthopedic device to the fasteners;

performing an orthopedic procedure using the orthopedic device;

removing the orthopedic device and fasteners from the patient; and closing the incision, without detaching the bone anchors from the bone.

* * * * *